US007062421B2

(12) United States Patent
Jacobson et al.

(10) Patent No.: US 7,062,421 B2
(45) Date of Patent: Jun. 13, 2006

(54) METHOD FOR PREDICTING ADHESIVE INTERACTIONS USING MOLECULAR MODELING

(75) Inventors: Solomon Jacobson, Berkeley Heights, NJ (US); Rajeev Farwaha, Belle Mead, NJ (US); Sharon P. Lee, Plainsboro, NJ (US)

(73) Assignee: Celanese International Corporation, Dallas, TX (US)

( * ) Notice: Subject to any disclaimer, the term of this patent is extended or adjusted under 35 U.S.C. 154(b) by 736 days.

(21) Appl. No.: 10/174,217

(22) Filed: Jun. 17, 2002

(65) Prior Publication Data

US 2003/0158717 A1    Aug. 21, 2003

Related U.S. Application Data

(60) Provisional application No. 60/358,903, filed on Feb. 21, 2002.

(51) Int. Cl.
*G06G 7/58* (2006.01)

(52) U.S. Cl. .............................. 703/12; 156/64; 356/35

(58) Field of Classification Search .................. 703/12, 703/7; 356/32, 35; 156/64
See application file for complete search history.

(56) References Cited

U.S. PATENT DOCUMENTS

| | | | | |
|---|---|---|---|---|
| 4,319,032 | A | | 3/1982 | Sandri et al. ................ 548/320 |
| 4,617,364 | A | | 10/1986 | Sekmakas et al. ........... 526/263 |
| 5,438,402 | A | * | 8/1995 | Gupta ........................ 356/35.5 |
| 5,496,907 | A | | 3/1996 | Dochniak .................... 528/73 |
| 5,575,868 | A | * | 11/1996 | Mann ........................... 156/64 |
| 6,031,041 | A | | 2/2000 | Chung et al. ................ 524/507 |
| 6,347,284 | B1 | * | 2/2002 | Ohira et al. .................. 702/41 |
| 6,544,650 | B1 | * | 4/2003 | Iwamoto ..................... 428/413 |
| 6,921,722 | B1 | * | 7/2005 | Ogure et al. ................. 438/708 |

* cited by examiner (Continued)

FOREIGN PATENT DOCUMENTS

WO    WO 97/49685    12/1997

OTHER PUBLICATIONS

Farwaha, Rajeev; Lee, Sharon; and Jacobson, Solomon H.; "Molecular Modeling of Adhesion Promoting Monomers for Coatings", Feb. 21-23, 2001.

*Primary Examiner*—Albert W. Paladini
(74) *Attorney, Agent, or Firm*—Michael W. Ferrell

(57) ABSTRACT

This invention relates to a process for using computerized molecular interaction modeling to predict the adhesive interactions between a substrate and a polymer. The molecular modeling method may be used to predict and select optimal adhesion promoting monomers for use in latex polymer coatings, providing the best wet adhesion to alkyd-coated substrates. The molecular modeling method could also predict substrate polymer pairs having the least affinity, and thus the most useful as a release liner. The method involves the steps of:

a) identifying interacting chemical segments on both the surface and the polymer;
b) generating models of the interacting segments, said models describing the spatial relationship of each atom in the segment and the connectivity between the atoms;
c) merging the models of each surface segment with each polymer segment to describe each possible interacting surface/polymer pair;
d) generating several hundred random configurations for each surface/polymer pair merged models, by choosing random values for the six spatial variables, that describe the relative orientations of two objects;
e) optimizing the atomic coordinates of each surface/polymer segment interaction model by calculating the minimum of the molecular potential energy;
f) computing the pair interaction energy for each merged model pair;
g) averaging the pair interaction energies; and
h) comparing the average pair interaction energies of each surface/polymer pair to choose the best pair for the intended application.

5 Claims, 6 Drawing Sheets

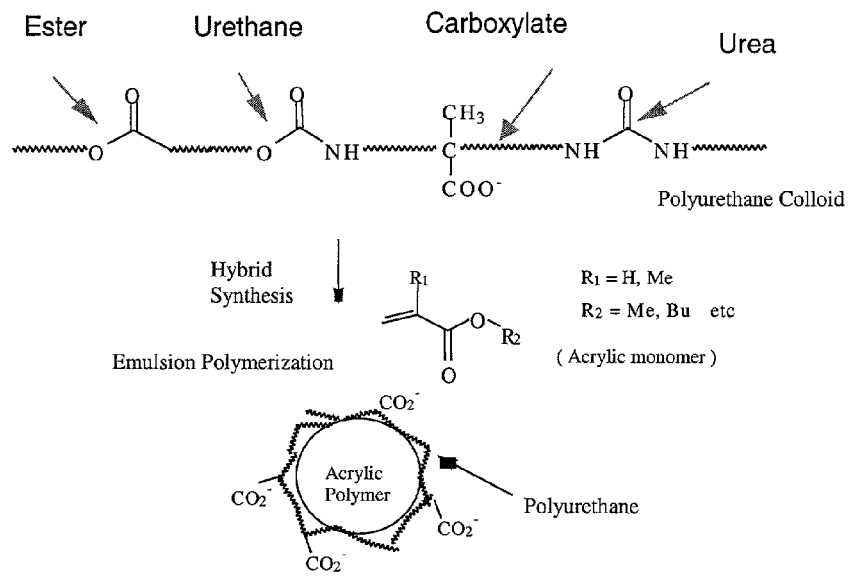
Figure 2. Polyurethane-Acrylic Hybrid
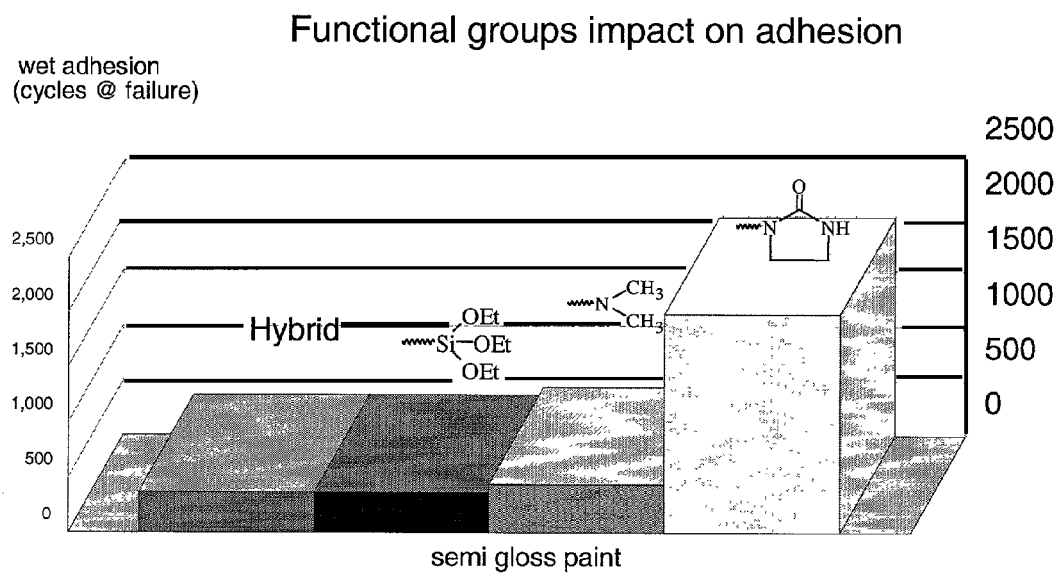
Figure 3. Effect of incorporating adhesion promoting monomer in acrylic polymer

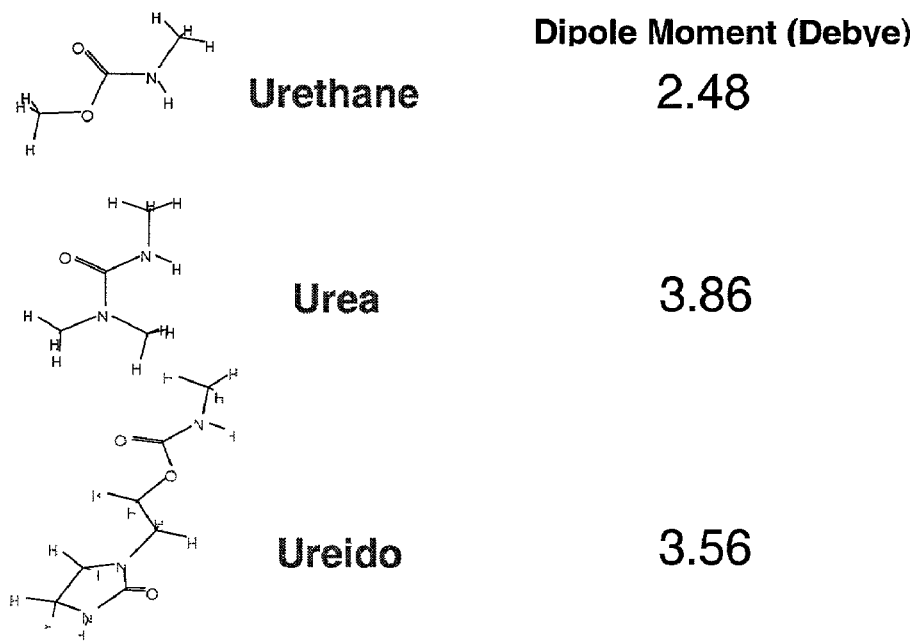
Figure 4. Model Compound and Computed Dipole Moment
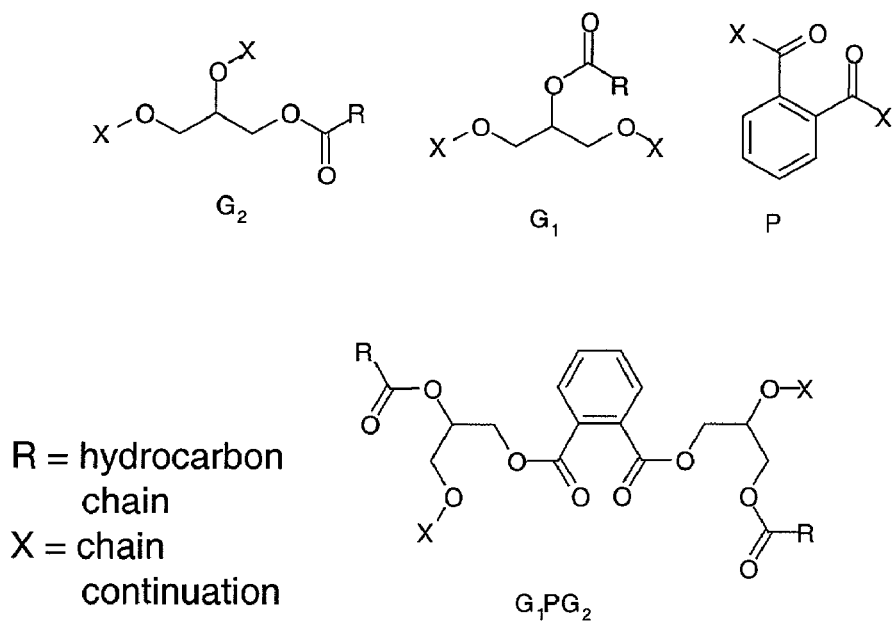
R = hydrocarbon chain
X = chain continuation
Figure 5. Alkyd Model

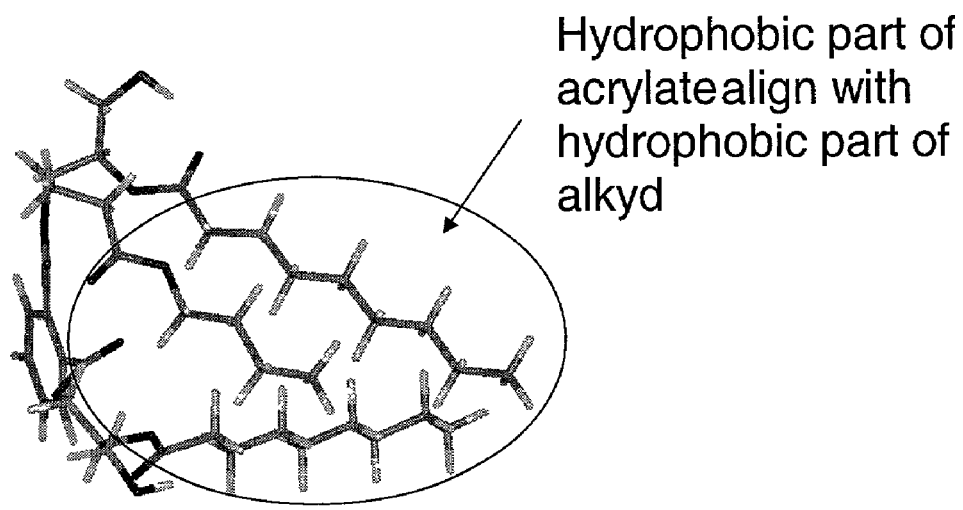
Figure 6. ButylAcrylate Alkyd Pair
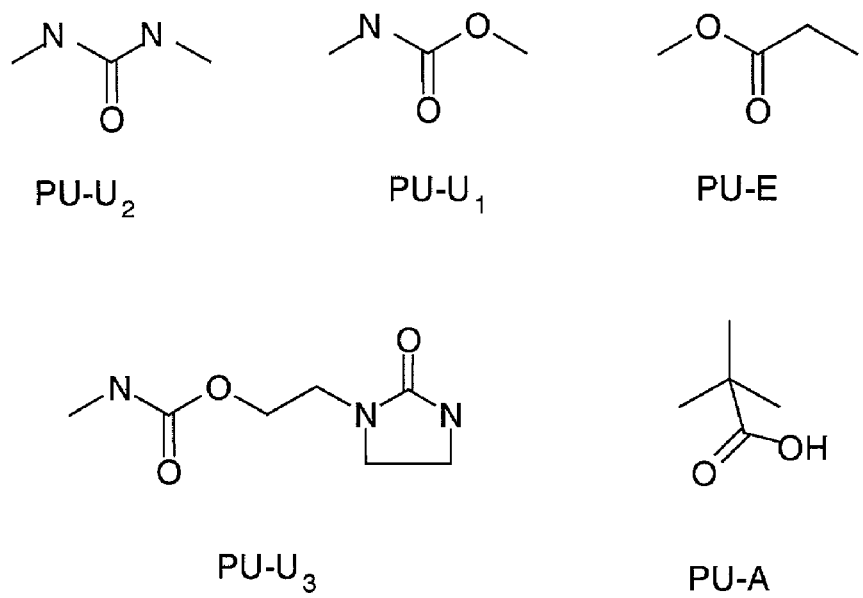
Figure 7. Polyurethane Segment Model

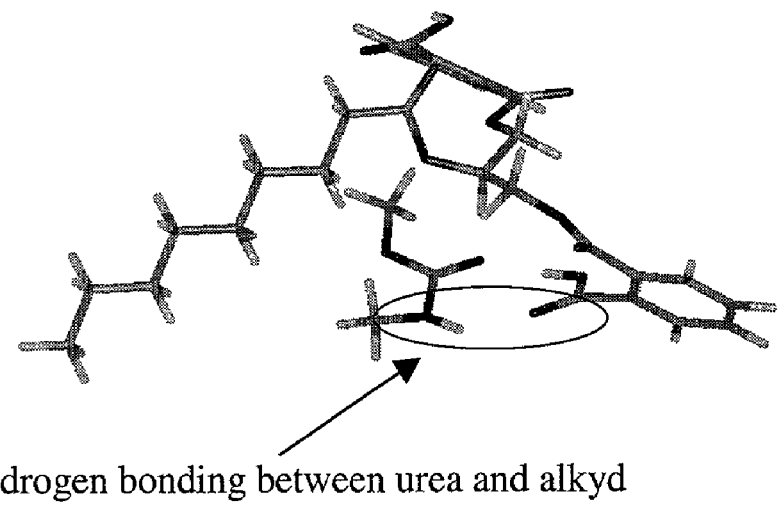
Hydrogen bonding between urea and alkyd
Figure 8. Structure of Urea-Alkyd Pair Configuration
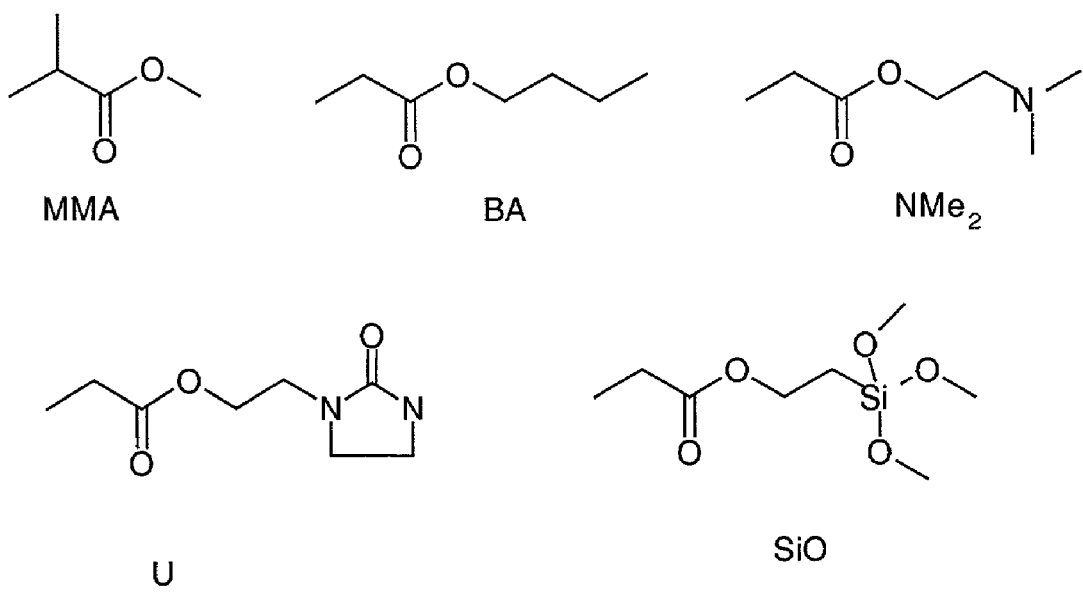
Figure 9. Acrylic Model Structures

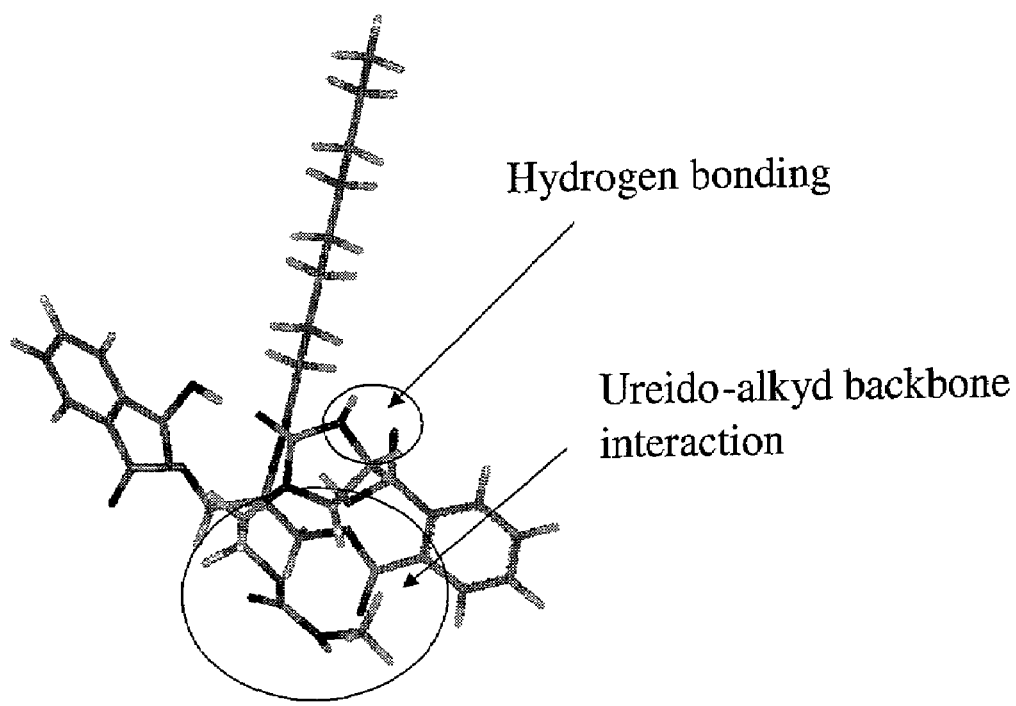
Figure 10. The Structure of Ureido-Alkyd Pair Configuration

METHOD FOR PREDICTING ADHESIVE INTERACTIONS USING MOLECULAR MODELING

This application is based on provisional U.S. patent application No. 60/358,903, entitled "Method For Predicting Adhesive Interactions Using Molecular Modeling", filed on Feb. 21, 2002, the priority of which is hereby claimed.

FIELD OF THE INVENTION

This invention relates to a process for using computerized molecular interaction modeling to predict the adhesive interactions between a substrate and a polymer. In particular the molecular modeling method may be used to predict and select adhesion promoting monomers for use in polymer coatings. A specific example is the selection of latex polymers providing the best wet adhesion to alkyd-coated substrates. The molecular modeling method could also predict the substrate and polymer having the least affinity, and thus the most useful as a release liner.

BACKGROUND OF THE INVENTION

Latex-based paints have captured a significant portion of the indoor and outdoor paint market as a result of many advantages that such paints have over solvent-based products. The main advantages of latex-based paints include easy clean-up, low-odor and fast dry.

The term wet-adhesion is used in the paint industry to describe the ability of the paint to retain its adhesive bond under wet conditions. Good wet adhesion is well known in solvent-based paints, but water-based paints tend to lose adhesion in wet or humid environments. The use of water based emulsion polymer systems as protective and decorative coatings on previously painted oil based substrates, has become wide spread. However, there is a great need for improving the adhesion of water based coatings on oil based substrates.

Many efforts have been devoted in recent years to improving the wet adhesion of latex paints on previously painted alkyd substrates. This effort has involved attempts to optimize various paint formulation parameters, such as pigment types, dispersant types, surfactants and coalescing agents. Significant improvement in wet adhesion properties has been observed through modification of the polymer backbone of the latex binder with amine, amide or ureido functionality, U.S. Pat. Nos. 5,496,907; 4,617,364; and 4,319,032. In particular, cyclic ureido compounds have been described as imparting improved wet adhesion behavior, WO 97/49685. While other functionalities have also been known to improve wet adhesion, incorporating the ureido functionality on the polymer backbone has a much more significant impact on the wet adhesion properties of water based paints on alkyd substrates.

The precise mechanism for the wet adhesion of latex based coatings to alkyd based substrates has not been reported in the literature. In "Development of Ureido Functional Monomers For Promoting Wet Adhesion in Latex Paints", R. W. Kreis, et al., the authors have suggested possible contributing factors for good wet adhesion of water based coatings on oil based substrates; i.e., 1) Anionic-Cationic interactions—Most of the substrates exhibit a net negative charge. By incorporating potentially cationic monomers, enhanced adhesive interactions can be provided between the functional group modified latex based coating and the negatively charged alkyd substrate. 2) Polar Interactions—Functional monomers can influence the degree of interaction between a latex film and the substrate. This could occur due to dipole interactions or hydrogen bonding. 3) Specific Bonding—A chelation type interaction between the latex binder and the substrate. 4) Interfacial Tension—Modification of the latex polymer with the appropriate functionalities can lower the interfacial tension between the polymer film and the substrate, thus enhancing the intimacy of contact.

The effects of various functional groups on wet adhesion were examined by making polyurethane-acrylic hybrid polymers containing different functional monomers, and then formulating them into a semi-gloss paint formula. Results obtained with functional monomers copolymerized with an acrylic latex were compared to systems with the functional monomer incorporated in the polyurethane backbone, and to systems without any functional monomer. The polyurethane-acrylic hybrids, with and without wet adhesion monomers, were prepared as disclosed in U.S. Pat. No. 6,031,041, incorporated herein by reference. A schematic representation of the resulting structure of these polyurethane-acrylic hybrids is shown in FIG. 2.

The wet adhesion properties of a polyurethane-acrylic hybrid without functional monomer were compared to a typical blended dispersion. Similar wet adhesion performance was obtained for the hybrid and the blend. The hybrid failed after 370 cycles, while the blend failed after 350 cycles Hybrid dispersions were prepared with the ureido group attached to the acrylic latex. Significantly better wet adhesion was observed. The film did not fail until 2000 cycles, compared to 370 cycles obtained for the hybrid without any functional monomers. A second ureido hybrid was prepared, but in this case, the ureido group was incorporated into the polyurethane backbone. This system also exhibited excellent wet adhesion, and did not fail until 1500 cycles.

Finally, hybrid dispersions were prepared with dimethylaminoethyl methacrylate and silane functional monomer attached to the acrylic latex, instead of the ureido functional monomer. The wet adhesion results for the dimethlyamine functionality and for the silane monomer were compared to the results obtained for the ureido functionality. These results are shown in FIG. 3. This plot shows that the silane functionality did not significantly improve the wet adhesion (380 cycles to failure for the silane system compared to 370 for the hybrid without functional monomer). A slight improvement in wet adhesion was observed for the hybrid containing the dimethylamine functional monomer (450 cycles to failure); however, the improvement was not nearly as large as that obtained with the ureido functional monomer (2000 cycles to failure). The surfactant stabilized acrylic latex resulted in 280 cycles.

Molecular modeling provides detailed information about molecular structure, electronic structure and molecular interactions. Therefore, molecular modeling can be used to determine the importance of these effects and may be able to explain some of the observed wet adhesion behavior.

In order to compare the polarity of the various functional groups in the polyurethane dispersion, high quality electronic structure calculations were performed on models of the various chemical moieties found in the polyurethane. The structures of the model compounds are shown in FIG. 4. The dipole moments of a urea, urethane and ureido group were computed and compared.

The molecular geometry and electronic structure of the model compounds were obtained using ab initio local density functional quantum mechanics. This was calculated using the Becke-Perdew-Wang (BPW) functional within the DMOL computer program, available from Accelrys Inc. A double numeric polarization basis set was also used in all calculations. Partial atomic charges, bond orders and dipole moments were all obtained using the DMOL quantum mechanics computer program.

The computed values of the dipole moments of the urethane, urea and ureido model compounds are 2.48, 3.86 and 3.56 Debyes, respectively. These results indicate that the ureido group is slightly more polar than the urethane group, but is less polar than a urea group. Therefore, molecular polarity alone does not explain the improved wet adhesion imparted by the ureido functionality. A more detailed modeling approach that simulates polymer-alkyd molecular interactions is required.

Surprisingly it has been found that a molecular model based on molecular interaction modeling can accurately predict the adhesive results of the tested systems. This modeling method may be used to predict the adhesive interactions between any polymer and a surface. The method of the present invention was presented at the International Waterborne, High-Solids, and Powder Coatings Symposium in the paper "Molecular Modeling of Adhesion Promoting Monomers for Coatings", Farwaha, et al, 2001.

SUMMARY OF THE INVENTION

The present invention is directed to a computerized molecular modeling method for predicting the adhesive strength between a surface and a polymer. The model makes use of calculations of the internal molecular energy of functional segments of a surface and a polymer. The method for predicting adhesive strength of a polymer involves the steps of:
 a) identifying interacting chemical segments on both the surface and the polymer;
 b) generating models of the interacting segments, said models describing the spatial relationship of each atom in the segment and the connectivity between the atoms;
 c) merging the models of each surface segment with each polymer segment to describe each possible interacting surface/polymer pair;
 d) generating several hundred random configurations for each surface/polymer pair merged models, by choosing random values for the six spatial variables, that describe the relative orientations of two objects;
 e) optimizing the atomic coordinates of each surface/polymer segment interaction model by calculating the minimum of the molecular potential energy;
 f) computing the pair interaction energy for each merged model pair;
 g) averaging the pair interaction energies; and
 h) comparing the average pair interaction energies of each surface/polymer pair to choose the best pair for the intended application.

A high average pair interaction energy indicates strong adhesive interactions between the surface/polymer segments. A low average pair interaction energy indicates weak adhesive interactions between the surface/polymer segments.

BRIEF DESCRIPTION OF THE DRAWINGS

The invention is described in detail below with reference to the following drawings:

FIG. 2 is a schematic diagram illustrating the structure of polyurethane-acrylic hybrid polymers;

FIG. 3 is a graph comparing the wet adhesion results for different functionalized acrylic polymers;

FIG. 4 is a diagram showing the structures of chemical moieties found in polyurethane and their respective dipole moments;

FIG. 5 is a diagram illustrating the structures of possible chain segments in alkyd polyester polymers;

FIG. 6 is a computer model illustrating the structure of a typical acrylic-alkyd pair configuration;

FIG. 7 is a diagram illustrating the structures of possible chain segments for a polyurethane resin;

FIG. 8 is computer model illustrating the structure of a typical urethane-alkyd pair configuration;

FIG. 9 is a diagram illustrating the structures of possible chain segments for an acrylic resin; and FIG. 10 is a computer model illustrating the structure of at typical ureido-alkyd pair configuration.

DETAILED DESCRIPTION OF THE INVENTION

Figure 1:
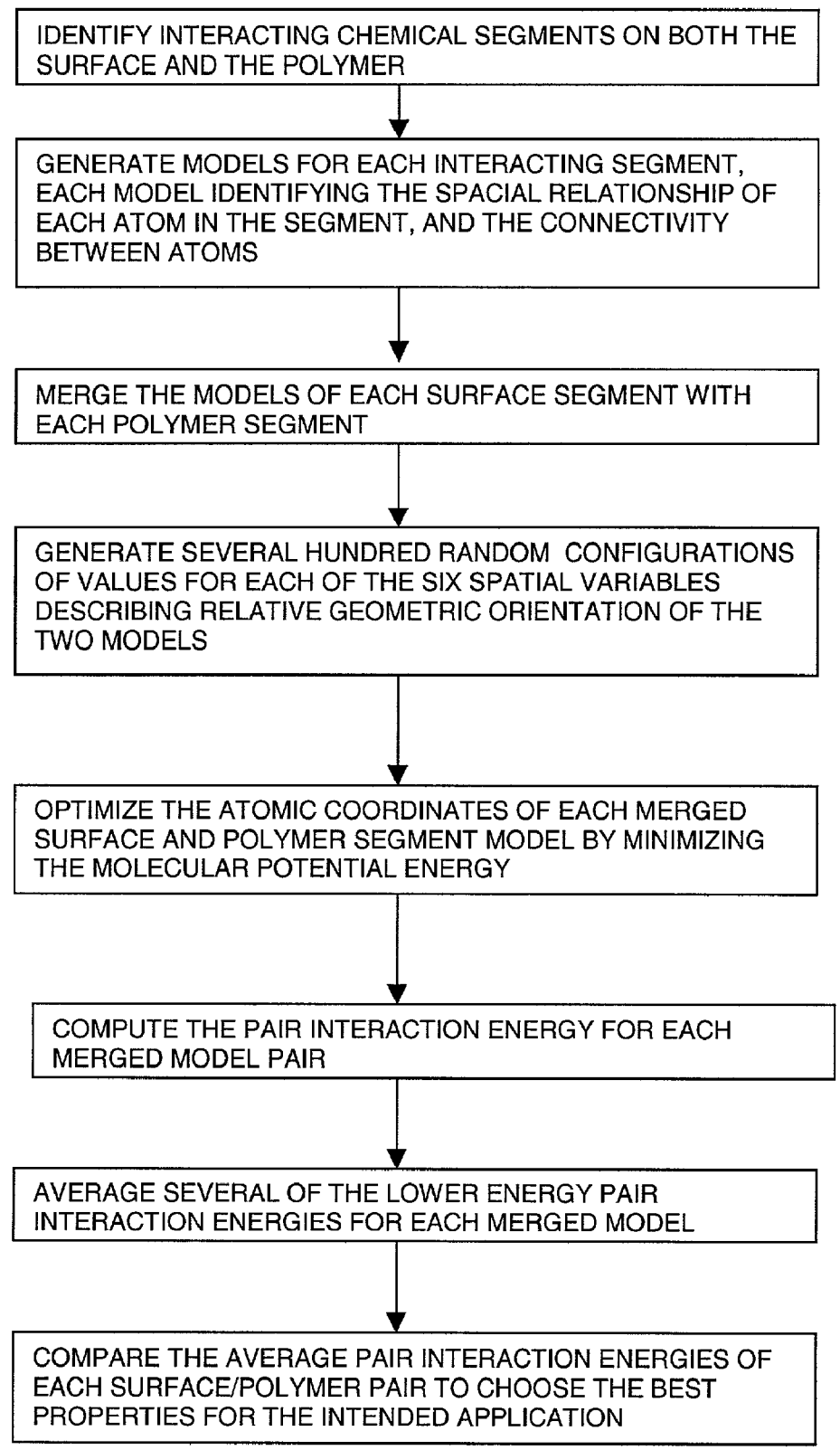
FIG. 1 is a flow chart outlining a method for predicting the adhesive interaction between a surface and a polymer.

The method for predicting the adhesive strength between a surface and a polymer as described herein may be used for any surface and any polymer. The method will be illustrated in terms of an alkyd-coated surface and an acrylic polymer. Other systems to which the method has been applied are described in the Examples. One of skill in the art will recognize still other systems in which adhesive strength (high or low) and other molecular interactions between polymers and surfaces is a concern, and may apply the method taught by the present invention to predict adhesive strength, or lack thereof, in such other systems.

The molecular model used in the present invention to predict the adhesive interaction between a surface and a polymer is based on calculations of the internal molecular energy of molecules. The internal molecular energy can be represented as a sum of forces that correspond to the motions and interactions associated with molecular systems (e.g., bond rotation, stretching, bending and non-bonded interactions). Simulations using these energy functions are termed force field calculations and are described in detail in "Molecular Mechanics", U. Burkert, N. Allinger, American Chemical Society, Wshington, DC, 1982. The equations used to describe the molecular potential in a force filed simulation involve a sum of molecular energy functions:

$$E = E_{Intramolecular} + E_{Intermolecular} \tag{1A}$$

where;

$$E_{Intramolecular} = E_{bond\ stretching} + E_{bond\ bending} + E_{torsional\ bond\ rotation} + \tag{1B}$$

and;

$$E_{intermolecular} = \Sigma j (E_{electrostatic} + E_{van\ der\ Waals}) \tag{1C}$$

The sum j in equation (1C) runs over all the neighboring atoms in the system. Since $E_{Intermolecular}$ contains explicit representations for electrostatic forces and van der Waals forces, this method is ideally suited to examine the role of electrostatic interactions, hydrogen bonding and molecular binding in adhesion phenomena.

The method of the invention involves the steps of:
 a) identifying interacting chemical segments on both the surface and the polymer;
 b) generating models of the interacting segments, said models describing the spatial relationship of each atom in the segment and the connectivity between the atoms;

c) merging the models of each surface segment with each polymer segment to describe each possible interacting surface/polymer pair;

d) generating several hundred random configurations for each surface/polymer pair merged models, by choosing random values for the six spatial variables, that describe the relative orientations of two objects;

e) optimizing the atomic coordinates of each surface/polymer segment interaction model by calculating the minimum of the molecular potential energy;

f) computing the pair interaction energy for each merged model pair;

g) averaging the pair interaction energies; and h) comparing the average pair interaction energies of each surface/polymer pair to choose the best pair for the intended application.

The first step is to identify the interacting chemical segments on both the surface and the polymer. For example, in an acrylic polymer, butyl acrylate (BA) and methylmethacrylate (MMA) monomers would have the structures:

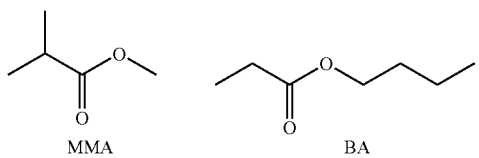

MMA            BA

Alkyd substrates are polyesters with a mixture of many different monomers. An ideal alkyd is made from 1 mole of phthalic anhydride (PA), 1 mole of glycerol and 1 mole of linoleic acid. In an ideal alkyd, the linoleic acid-glycerol combination can be considered as a single polymer repeat unit. There are two possible molecular geometries for this combination: 1) the linoleic acid is attached to the middle of the glycerol; or 2) the linoleic acid is on the end of the glycerol. We refer to these geometries as $G_1$ and $G_2$, respectively. When this linoleic acid-glycerol combination is reacted with the PA to form the polyester, five possible chain segments occur. These are $G_1$-PA-$G_1$, $G_1$-PA-$G_2$, $G_2$-PA-$G_2$, PA-$G_1$-PA and PA-$G_2$-PA. The structures of $G_1$, $G_2$ and PA are shown in FIG. 5. A sample triad segment is also shown in FIG. 5.

The molecular interactions between a typical acrylic polymer and as alkyd substrate can be predicted from molecular models of the interacting segments. A molecular model consists of the three-dimensional coordinates of a small, but representative, portion of the molecular system. The model should represent the key elements of the phenomena of interest. Since, in this example, we are comparing the effects of various chemical moieties on adhesion, a model that considers local molecular interactions is required. Therefore, a modeling scheme aimed at determining the interactions between a small segment of polymer and a small segment of alkyd substrate is developed. The modeling procedure is similar to the methods used to predict polymer miscibility and phase behavior, S. Jacobson, et al. *Advanced Materials,* 4(3), 198, 1992. The models may be generated by a computer software program, such as INSIGHT molecular modeling software available from Accelrys, Inc. One model is produced for each molecular segment. The models are then merged, using the INSIGHT merge function, to describe each surface/polymer pair. From these merged model pairs, several hundred random configurations are generated for pairs of each monomer with each of the five alkyd models described above. The random configurations may be generated by a program such as the FLEXIBLEND option on the INSIGHT modeling software. Preferably at least 200 random pairs are generated for each model, more preferably from 200 to 1000, and most preferably from 200 to 500 from a practical standpoint. The atomic coordinates of the model are optimized by minimizing the molecular potential energy, calculated by using Equation 1 (A) and running on a computer program such as the DISCOVER molecular modeling program from Accelrys. The average molecular interaction energy of each alkyd pair model was determined from the 50 lowest energy configurations. These five average energy values were then averaged, leading to a single average alkyd interaction energy for each monomer. The results for MMA-alkyd and BA-alkyd are 8.1 kcal/mole and 10.0 kcal/mole, respectively. These values will serve as a reference point and can be used to compare the values obtained from modeling other monomers and functional groups. The structure of a typical acrylic-alkyd pair configuration is shown in FIG. 6. This FIG. shows that the butyl group of the acrylate interacts with the hydrocarbon part of the alkyd, and the acrylate part of the monomer interacts with the polyester backbone of the alkyd.

This modeling scheme can be systematically applied to several different monomers and chemical species. Comparison of the computed molecular interaction energies can be used to rank various monomers for alkyd affinity. Larger values of the pair molecular interaction energy imply better alkyd affinity.

The wet adhesion and molecular interaction energy results strongly suggest that wet adhesion performance is related to the molecular interactions between the alkyd substrate and the monomer with the strongest molecular interaction energy. Adding molecular functionality to the system with stronger alkyd molecular interaction energies improves the observed wet adhesion performance.

It is interesting to observe that the adhesive enhancement does not depend on the relative amounts of the functional groups. A small amount of functional monomer can have a dramatic effect on wet adhesion. Levels of functional groups of 0.2 to 2 percent are preferred. This suggests that the wet adhesion behavior obeys a "strongest link" mechanism. Good wet adhesion can be achieved with a few strong "links" between the polymer film and the alkyd surface. That is, the wet adhesion performance will depend on the strength of the strongest surface interaction between localized groups, rather than the overall surface interaction energy.

The wet adhesion performance showed an exponential dependence on the computed monomer-alkyd interaction energy. This effect does not depend strongly on the amount of functional monomer present, suggesting that a few strong localized polymer-surface contacts are controlling wet adhesion. Molecular modeling proved to be a useful tool in understanding the reasons for the good wet adhesion imparted by the ureido functional monomer in terms of polymer-alkyd molecular interactions.

The method of the invention can also be used to predict and select substrate and polymer pairs having low adhesive interactions. Such predictions are useful in selecting release liners and other applications in which low molecular interactions are desired.

The method of the present invention is not restricted to any particular substrate, nor to any specific type of polymer. Any substrate having some functionality and requiring specific molecular interactions could be modeled by this method. Of particular interest are substrates that are generally difficult to adhere to, such as polyesters, polycarbonates, and plastics, where van der Waals forces and electrostatic interactions are important, rather than covalent bonding. The method could be applied also to wood and paper substrates.

The following examples are presented to further illustrate and explain the present invention and should not be taken as limiting in any regard.

EXAMPLE 1

Alkyd-Polyurethane

The molecular model described above was applied to the interaction between an alkyd-coated substrate and a polyurethane. The ideal structure of the polyurethane dispersion is shown in FIG. 1. Here, the possible chain segments include ester, carboxylic acid, urea and urethane. Functionalized polyurethane also contains ureido functional monomer. These chain segments are referred to as PU-E, PU-A, PU-$U_1$, PU-$U_2$ and PU-$U_3$, respectively. The structures of these models are shown in FIG. 7.

These acrylate results were compared to results for various polyurethane segments. Average alkyd-polyurethane segment interaction energies were obtained as described above. The computed average interaction energies for acid (PU-A), ester (PU-E), urethane (PU-$U_1$) and urea (PU-$U_2$) are 11.5, 7.1, 13.2 and 11.9 kcal/mole, respectively. Generally these results are higher than values obtained for the acrylates, indicating that the polyurethane has a greater affinity for an alkyd surface compared to the acrylic polymer.

The structure of a urethane-alkyd pair configuration is shown in FIG. 8. Here the hydrogen bonding between the —NH group of the urethane and the —C═O group of the alkyd can be seen. This hydrogen bonding may be responsible for the increased molecular interaction energy compared to the acrylic polymer.

A slight improvement in wet adhesion was achieved for the polyurethane-acrylic hybrid compared to the surfactant stabilized acrylic system. The wet adhesion values were 370 and 280 cycles, respectively. The largest alkyd molecular interaction energy for the all acrylic system was 10.0 kcal/mole for butyl acrylate-alkyd interactions. The largest molecular interaction energy in the polyurethane hybrid was 13.2 kcal/mole for the urea-alkyd interactions.

EXAMPLE 2

Alkyd-Adhesion Promoting Monomers

The molecular modeling method of the invention was applied to an alkyd surface and adhesion-promoting monomers of a polymer, in the manner described above. The acrylic latexes studied here are composed of mainly butyl acrylate and methyl methacrylate. Small amounts of functional monomer can also be included in the composition. These monomers include amine, silane and ureido functionalities. Here, the model segments are referred to as BA, MMA, $NMe_2$, SiO and U, respectively. The structures of these models are shown in FIG. 9.

Molecular interactions between alkyd and the functional monomers were examined. The computed molecular interaction energies for silane (SiO), amine ($NMe_2$), and ureido (U) are 12.6, 13.7, and 16.3 kcal/mole, respectively. These functional groups have stronger molecular interactions compared to the typical acrylic latex polymer, with the ureido group showing the strongest alkyd molecular affinity. FIG. 10 shows the structure of a ureido-alkyd pair configuration. This figure shows that the ureido group interacts mostly with the backbone of the alkyd polyester. Here, multiple regions of hydrogen bonding are possible. These hydrogen bonds, plus a favorable spatial overlap, are most likely responsible for the strong ureido-alkyd molecular interactions.

The wet adhesion of acrylic-polyurethane hybrid system was improved when functional monomers with stronger alkyd molecular interactions were included. For example, including an amine functionality with a slightly higher molecular interaction energy of 13.7 kcal/mole, compared to the 13.2 kcal/mole of the urea functionality, improved the wet adhesion from 370 to 450 cycles. A dramatic improvement of wet adhesion behavior, i.e., 2000 cycles, was observed when the ureido functional monomer was included. This monomer also showed a significant increase in the alkyd molecular interaction energy: 16.3 kcal/mole, compared to 13.2 computed for the urea functionality in the polyurethane backbone. It is interesting to note that the observed improvement in wet adhesion increases nearly exponentially with increasing alkyd-functional group interaction energy.

What is claimed is:

1. A method for predicting the adhesive interaction between a surface and a polymer, comprising the steps of:
    a) identifying interacting chemical segments on both the surface and the polymer;
    b) generating models of the interacting segments, said models describing the spatial relationship of each atom in the segment and the connectivity between the atoms;
    c) merging the models of each surface segment with each polymer segment to describe each possible interacting surface/polymer pair;
    d) generating several hundred random configurations for each surface/polymer pair merged models, by choosing random values for the six spatial variables, that describe the relative orientations of two objects;
    e) optimizing the atomic coordinates of each surface/polymer segment interaction model by calculating the minimum of the molecular potential energy;
    f) computing the pair interaction energy for each merged model pair;
    g) averaging the pair interaction energies; and
    h) comparing the average pair interaction energies of each surface/polymer pair to choose the best pair for the intended application.

2. The method of claim 1 comprising choosing the surface/polymer segment pair having the largest average pair interaction energy, for applications requiring the greatest adhesive strength.

3. The method of claim 1 comprising choosing the surface/polymer segment pair having the smallest average pair interaction energy, for applications requiring the least adhesive strength.

4. The method of claim 1 wherein the segments of the polymer comprise one or more adhesion promoting monomers.

5. The method of claim 1 wherein said surface comprises an alkyd-coated substrate.

* * * * *